(12) United States Patent
Fregoso

(10) Patent No.: US 6,611,110 B1
(45) Date of Patent: Aug. 26, 2003

(54) PHOTOPOLYMERIZATION APPARATUS

(75) Inventor: Gilbert Fregoso, Hamilton, MT (US)

(73) Assignee: Design Rite, LLC, Walnut, CA (US)

( * ) Notice: Subject to any disclaimer, the term of this patent is extended or adjusted under 35 U.S.C. 154(b) by 0 days.

(21) Appl. No.: 09/907,140

(22) Filed: Jul. 17, 2001

Related U.S. Application Data

(63) Continuation-in-part of application No. 09/765,897, filed on Jan. 16, 2001
(60) Provisional application No. 60/273,105, filed on Mar. 2, 2001.

(51) Int. Cl.[7] .............................................. H05B 37/02
(52) U.S. Cl. ....................... 315/224; 315/291; 315/225; 315/360; 362/800; 362/294; 433/29; 433/27
(58) Field of Search ................................ 315/112, 115, 315/117, 224, 291, 225, 292, 307, 360, 362, 294; 362/119, 293, 800, 294, 231; 433/27, 29, 31

(56) References Cited

U.S. PATENT DOCUMENTS

| | | | |
|---|---|---|---|
| 4,384,317 A | * 5/1983 | Stackpole | ................... 136/291 |
| 5,233,283 A | 8/1993 | Kennedy | |
| 5,312,249 A | 5/1994 | Kennedy | |
| 5,420,768 A | 5/1995 | Kennedy | .................... 362/119 |
| 5,634,711 A | 6/1997 | Kennedy et al. | ............ 362/119 |
| 6,102,696 A | 8/2000 | Osterwalder et al. | ......... 433/29 |
| 6,159,005 A | 12/2000 | Herold et al. | ................. 433/29 |
| 6,333,602 B1 | * 12/2001 | Kayser | ....................... 315/112 |
| 6,419,483 B1 | * 7/2002 | Adam et al. | ................ 433/215 |

FOREIGN PATENT DOCUMENTS

EP   0 567 280 A2   4/1993

OTHER PUBLICATIONS

Sherman, Len (Oct. 23, 1997) Logic Power Drives High–Intensity LEDs *Ideas for Design* vol. 2328: 142 and 144.
Hoffart, Fran (Dec. 15, 1997) Series LED Driver Operates on 3–V Input *ideas for design* fol. 2328: 106 and 108.

\* cited by examiner

*Primary Examiner*—Haissa Philogene
(74) *Attorney, Agent, or Firm*—Saliwanchk, Lloyd & Saliwanchik

(57) ABSTRACT

A light-weight, portable photocuring device possesses a single light emitting diode (LED). The single LED backed with a heat sink is driven by a driving circuit and controlled by a timing circuit. A temperature monitor can be included in a closed loop to feed back and control the driver. Lenses and/or light guides in the device act to further direct the light.

28 Claims, 2 Drawing Sheets

PHOTOPOLYMERIZATION APPARATUS

This application is a continuation-in-part of U.S. patent application Ser. No. 09/765,897, filed Jan. 16, 2001. This application also claims priority to U.S. Provisional Patent Application Serial No. 60/273,105, filed Mar. 2, 2001. The disclosures of each of these applications are hereby incorporated by reference in their entirety, including all figures, tables, and drawings.

BACKGROUND OF THE INVENTION

A number of resins which are cured or polymerized in response to light are known. Perhaps the most familiar of these are resins or composites used in dental technology. Dental composites are used to fill cavities, bond abraded enamel and for many cosmetic applications. When irradiated with light, dental resins polymerize due to a metacrylate based curing mechanism. Photo-initiators, such as camphor quinone and phosphine oxide, start the curing process by absorbing a broad band within the blue spectral range. For example, camphor quinone has an absorption maximum of about 472 namometers (nm), while phosphine oxide has an absorption maximum of 430 nm.

Light of this wavelength can be generated by tungsten-halogen lamps, laser diodes or light emitting diodes (U.S. Pat. No. 6,159,005). In order to achieve light of sufficient intensity for photopolymerization when using light emitting diodes (LEDs), it is often necessary to employ a plurality of LEDs (U.S. Pat. No. 5,420,768, U.S. Pat. No. 5,634,711 and U.S. Pat. No. 6,102,696). Photocuring devices which utilize a plurality of LEDs consume a great deal of power and produce much heat. This increased energy requirement contributes to the weight and complexity of these devices. Further, complicated systems are needed to capture and focus the light from the multiple LEDs which reduce the efficiency of current devices.

From the foregoing, it is apparent that a light-weight, cool-running and efficient hand-held photocuring device is needed. This device preferably is powered by a self-contained source, for example, a simple battery, so that the device is portable and not encumbered with cords. The device should be light-weight so that it is easily maneuvered during delicate procedures and should run cool so as not to adversely affect the polymerization process by providing excess heat to the photopolymerization reaction.

All patents, patent applications, provisional patent applications and publications refered to or cited herein, are incorporated by reference in their entirety to the extent they are not inconsistent with the explicit teachings of the specification

SUMMARY OF THE INVENTION

A light-weight, portable photocuring device delivers light of sufficient intensity to cause photopolymerization using a single light emitting diode (LED). The single high powered LED is driven by a driving circuit controlled by a timing circuit. A heat sink on the LED is monitored by a thermal monitor. The device can be powered with a simple battery. The single LED can be positioned internally within the device or at the tip of the device. When placed internally, a system of one or more lenses and/or known light focusing means or light guides can be added to the device to further focus and intensify the light provided by the LED.

DETAILED DESCRIPTION OF THE INVENTION

Figure 1:
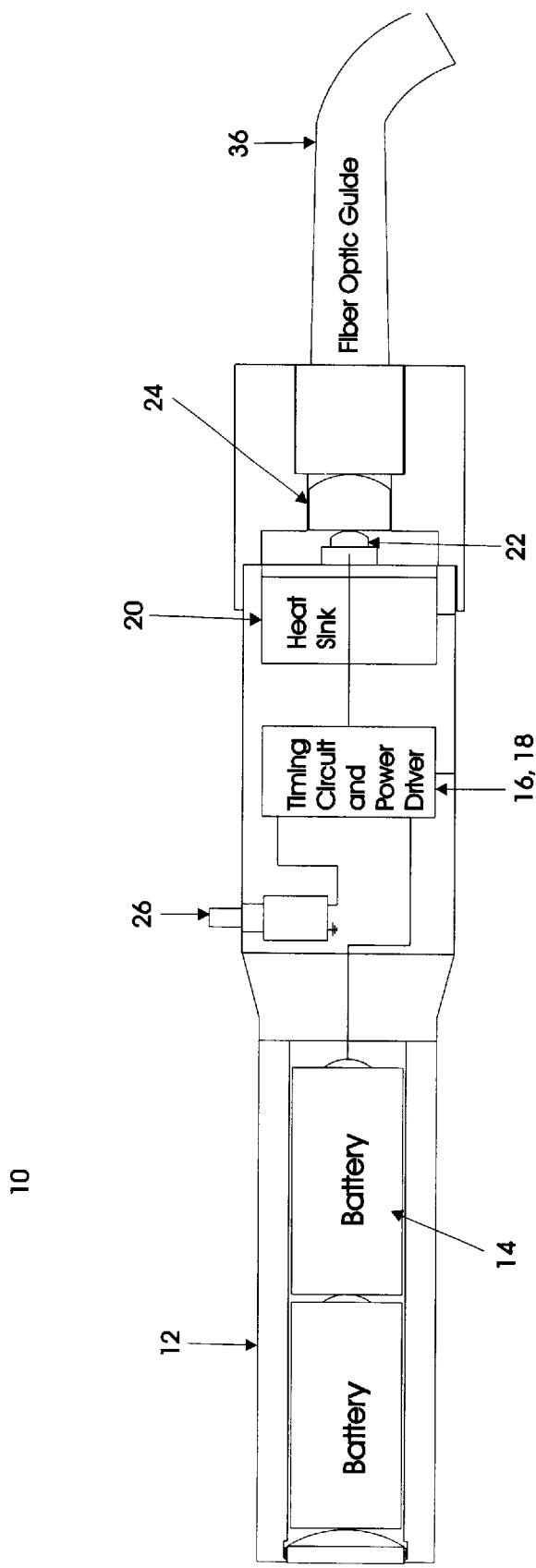
FIG. 1 is a cross-sectional view down the longitudinal axis of a preferred embodiment of the photopolymerization device of the subject invention.

A preferred embodiment of the apparatus of the subject invention is shown generally at 10 in FIG. 1. FIG. 1 shows a hand-held portable photocuring device that utilizes a single light emitting diode (LED). A housing 12 contains a power supply 14, i.e. batteries, a timing circuit 16, and LED power driver 18, a heat sink 20 and single high power LED 22. The housing can also contain, or be fitted with, a lens system 24 for focusing the light from the LED and a light guider 36. A momentary switch 26 can be placed on the exterior of the housing to activate the timing circuit.

The power source 14 provides power to a timing circuit and LED power driver. The power source can be one or more alkaline batteries, or rechargeable batteries, such as lithium ion or nickel metal hydride, or the device can be plugged into a wall socket. Batteries allow full maneuverability of the device because it is not restricted by a cord.

In a preferred embodiment, the timing circuit is an LM555 timing circuit. This CMOS based timing circuit requires little energy thus applying little draw to the battery and is extremely reliable. A momentary switch 26 starts the timing circuit which is set to run for a period of time. For example, the timing circuit can be set for between about 5 and 10 seconds.

An LED power driver 18 drives the LED 22. This power driver should be highly efficient. In a preferred embodiment, the LED power driver is that described in U.S. Patent application Ser. No. 09/765,897, filed Jan. 16, 2001, which application is hereby incorporated by reference. Briefly, the driver circuit comprises an inductive storage device, a switching regulator device, a rectifier and filter and, a current sensing device in a closed loop feedback system. An inductive storage device allows the LED to be driven with minimal voltage input. The switching regulator device monitors and regulates the power applied to the LED, protecting the diode.

In a specific embodiment, a power source provides DC current to an inductive storage device, such as an inductor. Preferably, the inductive storage device is wire wound with an inductance between about 22 and 220 micro henries. Wire wound inductors reduce resistance.

Current from the inductive storage device goes to a high speed switching converter and regulator device. The switching regulator device can be an integrated circuit (IC) having a reference voltage source, an oscillation circuit, a power MOSFET, and an error amplifier. In a preferred embodiment the switching regulator device is a CMOS PWM/PFM-control step-up switching regulator.

Energy in the inductive storage device is converted to AC current. Energy leaving the switching regulator device is likewise AC current. Accordingly, this AC current can be rectified and filtered to DC current through a rectifier and filter. A Schottky diode is a preferred rectifier and filter. A Schottky diode can provide a fast reverse recovery time and a low forward voltage drop. The rectified and filtered current is fed back to the switching regulator device where it can be controlled and monitored for the proper voltage output.

The rectified and filtered DC output is sent to a current sensing device, which controls the current sent to the LEDs.

In a specific embodiment, the current sensing device is a current driver and temperature compensation circuit having an error amplifier, a current sensing resistor, and at least two reference voltage resistors. In a particularly preferred embodiment, the current sensing device further comprises a transistor used as a power driver. The current sensing and temperature compensation circuit controls the temperature, protecting the light emitting diode from thermal runaway and allows the LED to be driven at or near maximum current without the LED being destroyed.

Figure 2:
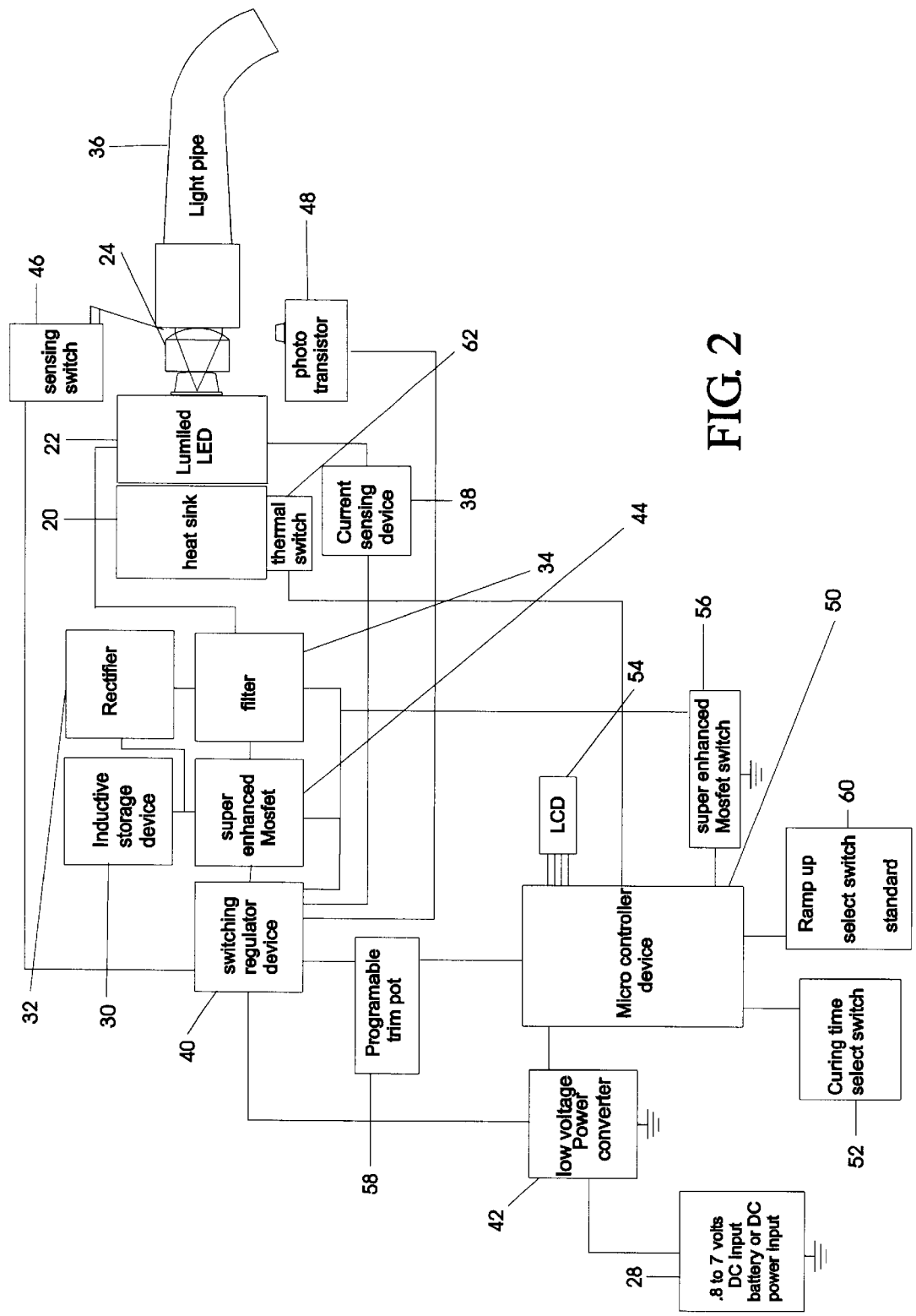
FIG. 2 is a cross-sectional view down the longitudinal axis of another preferred embodiment of the photopolymerization device of the subject invention.

Another specific embodiment of a preferred circuit is shown incorporated into the photocuring device of FIG. 2. In this circuit, the switching regulator device comprises a programmable reference voltage source and is driven by a low voltage power converter. The switching regulator device also has an external super enhanced MOSFET.

The DC power input 28 provides power to the inductive storage device 30. Within the inductive storage device 30 energy is transformed into AC current. The energy is converted from AC to DC current by a rectifier 32. Preferably, the rectifier is a Schottky diode. The current is then filtered at 34 before being applied to the LED 22. A current sensing device 38 feeds a signal reference voltage back to a switching regulator device 40 providing current load information for regulating the circuit. Preferably, the current sensing device 38 is a resistor having a resistance of less than about 15 ohms ($\Omega$).

The switching regulator device 40 monitors the signal from the current sensing device 38 and regulates the energy released into the circuit. In a specific embodiment, the switching regulator device 40 requires about 3 V of power. A low voltage power converter circuit 42 is introduced into the circuit to provide the power necessary to run the switching regulator device 40. Preferably, the low voltage power converter is capable of producing 3 V when supplied with as little as 0.8 V input. The converter circuit should further be capable of producing about 20 mA when supplied with the 0.8 V DC input. The low voltage power converter 42 supplies the 3 V necessary to power the switching regulator device 40. The switching regulator device 40 can incorporate a programmable reference voltage source, an oscillation circuit, and an error amplifier. An external super enhance MOSFET 44 is controlled by the switching regulator device 40 and loads the inductive storage device 30. The super enhanced MOSFET is a very efficient transistor and requires very little current to operate.

The photocuring apparatus of the subject invention further comprises a heat sink 20 (FIGS. 1 and 2). Preferably, the heat sink is aluminum. The heat sink can also be other means known in the art of dissipating heat or a combination thereof. The heat sink cools the single light emitting diode of the device.

The light emitting diode used in the apparatus of the subject invention is a high power LED 22. While a conventional LED can withstand a maximum current of 30 mA, a high power LED can withstand a maximum continuous current of about 1.5 A. High powered LEDs have a normal operating current of between about 350 mA and 500 mA. A specific example of such an LED is a LUMILED Power Light Source. Additionally, the LED used in the exemplified embodiments emits blue light of 470 nm. LEDs emitting other wavelengths of light can be used in the apparatus of the subject invention. For example, light of 430 nm is useful in some dental applications while light in the red spectra is useful for some dermal treatment applications.

Light from the LED can be focused by one or more culminating lenses 24 and further guided to the area of polymerization with a light guide 36. A normal LED emits light at an approximately 20° angle. The high powered LEDs used in the apparatus of the subject invention emit light at 120° angle. Thus a culminating lens is used to focus the emitted light into a narrow, useful, beam path. The lens can be made from glass or a plastic such as polycarbonate. The lens is ground or configured to focus the light emitted at 120° from the light emitting diode into a beam of about 8 mm. Light guides are known in the art and serve to deliver emitted light to the point of photopolymerization. Light guides useful according to the subject invention include a simple, glass or polycarbonate tube. Preferably, the guide should be opaque and be able to be sterilized, most preferably by autoclaving. Therefore, the waveguide tip of the unit can be removed and sterilized between patients. Other known waveguides include those having fiber optic bundles to direct emitted light to the tip of the device Additionally, the LED can be placed at the tip of the instrument so the light can be delivered directly to the surface of the tooth.

The specific embodiment of the photopolymerization device shown in FIG. 2 further includes features which enhance the safety and utility of the subject device. For example, sensing switch 46 acts as a safety switch wherein the device delivers maximum intensity only when the wafe guide 36 is seated on the culminating lens 24. A thermal switch 62 embedded in the heat sink provides feedback to the microcontroller 50 preventing the LED from overheating.

A phototransistor 48 measures stray light to determine if the device is providing an adequate light output. The phototransistor 48 acts as a simple radiometer operating at a preset valve in reference to the switching regulator device 40. Thus, the phototransistor 48 acts as a secondary back-up. The current sensing device of a preferred embodiment assures the LED is receiving proper current. The phototransistor assures the apparatus is delivering light of sufficient intensity. Should the LED begin to degrade, the phototransistor will detect the change in light intensity allowing the circuit to compensate for the loss. If the circuit is unable to compensate, the unit will be shut down.

A microcontroller 50 replaces the timing circuit of the device shown in FIG. 1. The microcontroller 50 times the illumination period for curing providing a selection of times, for example, from 5 seconds incrementally to 40 seconds, selected by the curing time select switch 52 and noted by a liquid crystal display 54. A super enhanced MOSFET 56 acts as the main power switch for the apparatus.

Combination of the microcontroller 50 and a programmable trim pot 58 allow adjustment of the output intensity of light current. A select switch 60 allows the user to choose full power immediately or to have the power ramp up from, for example, 0 to full power in a number of seconds. LED indicator lights can be installed on the select switch 60 to indicate the power selection. Likewise, audible signals can be provided indicating, for example, the start, one beep, and the finish two beeps of the curing cycle.

It is noted that previous devices employing a plurality of LEDs require much power to operate. The LEDs in these devices must be pulsed to achieve sufficient light intensity. The device of the subject invention employs an efficient circuit that provides direct current to the single LED. Because this LED is not pulsed, it is not stressed and therefore the circuit of the device of the subject invention contributes to the longevity of the LED.

Utilizing a high powered LED in the device of the subject invention allows that only a single LED is need be present in the device. In preferred embodiments, this LED is driven by circuits which supply continuous current to the LED. Application of continuous current reduces stress on the diode assuring its longevity. The LED could however be pulsed and deliver sufficient light. One skilled in the art is aware of how to convert a circuit to a pulsing circuit. Preferably, any pulsing circuit would have a current sensing device and perhaps a phototransistor to protect the LED and detect its eminent degradation.

It is estimated that between 4 and 6 percent of emitted light is lost with the addition of each lens to an LED. A lens captures and directs that light into an intensified usable beam. Prior devices which utilize a plurality of LEDs require a plurality of lenses. Much light is lost in these devices greatly reducing their efficiency. The device of the subject invention however utilizes only a single LED. The light from this LED can be focused using a single lens making the subject device for more efficient than those requiring multiple lights and lenses.

The simple, efficient driving circuit requires little energy to operate and provides sufficient power to drive a single high powered LED to the photocuring device of the subject invention. Further, only light emitted from a single LED must be focused within the subject device, thus little light is lost or wasted.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A photopolymerization apparatus comprising:
   a housing;
   one light emitting diode;
   a heat sink;
   a timing circuit;
   a driver circuit, wherein said driver circuit comprises an inductive storage device, a switching regulator device, a rectifier, a filter, and a current sensing device; and
   a means for applying power to said driver circuit.

2. The apparatus of claim 1, wherein said inductive storage device is wire wound with an inductance between about 22 and 220 micro henries, wherein said switching regulator device is a CMOS PWM/PFM-control step-up switching regulator, wherein said rectifier is a Schottky diode, and wherein said current sensing device is a current driver and temperature compensation circuit comprising an error amplifier, a current sensing resistor, at least two reference voltage resistors, and a transistor as a power driver.

3. The apparatus of claim 1, wherein said inductive storage device is wire wound with an inductance between about 22 and 220 micro henries.

4. The apparatus of claim 1, wherein said switching regulator device comprises:
   a reference voltage source;
   an oscillation circuit;
   an error amplifier; and
   a power MOSFET.

5. The apparatus of claim 1, wherein said switching regulator device is a CMOS PWM-PFM-control step-up switching regulator.

6. The apparatus of claim 1, wherein said rectifier is a Schottky diode.

7. The apparatus of claim 1, wherein said current sensing device is a current driver and temperature compensation circuit comprising an error amplifier, a current sensing resistor and at least two reference voltage resistors.

8. The apparatus of claim 7, wherein said current driver and temperature compensation circuit further comprises a transistor as a power driver.

9. The apparatus of claim 1, further comprising a low voltage power converter circuit.

10. The apparatus of claim 9, wherein said low voltage power converter circuit produces 3 to volts and 20 milliamps when supplied with at least 0.8 volts input.

11. The apparatus of claim 9, wherein said switching regulator device comprises:
    a programmable reference voltage source;
    an oscillation circuit; and
    an error amplifier.

12. The apparatus of claim 11, further comprising a super enhanced MOSFET.

13. The apparatus of claim 1, wherein said means for applying power is at least one battery.

14. The apparatus of claim 1, wherein said means for applying power is selected from the group consisting of: one or more AAA batteries, one or more AA batteries, one or more C batteries and one or more D batteries.

15. The apparatus of claim 1, further comprising a temperature monitor.

16. The apparatus of claim 1, further comprising at least one lens.

17. The apparatus of claim 1, further comprising a light guide.

18. The apparatus of claim 1, further comprising at least one lens and a light guide.

19. The apparatus of claim 18, further comprising a sensing switch for detecting the position of said light guide on said lens.

20. The apparatus of claim 1, further comprising a phototransistor for detecting stray light and providing feedback to said switching regulator device.

21. The apparatus of claim 1, wherein said timing circuit is an LM555 timing circuit.

22. The apparatus of claim 1, wherein said timing circuit is a microcontroller.

23. The apparatus of claim 22, further comprising a thermal switch which feedsback to said microcontroller.

24. The apparatus of claim 23, further comprising a programmable trim pot to allow power to be ramped up.

25. The apparatus of claim 1, wherein said circuit is at least about 70% to about 99% efficient.

26. The apparatus of claim 1, wherein said circuit is at least about 90% efficient.

27. The apparatus of claim 1, wherein said circuit is at least about 97% efficient.

28. The apparatus of claim 7, wherein said switching regulator device comprises a programmable reference voltage source, an oscillation circuit, and an error amplifier, and wherein said circuit further comprises a low voltage power converter circuit capable of producing 3 volts and 20 milliamps when supplied with a least 0.8 volts input and a super enhanced MOSFET.

* * * * *